United States Patent [19]

Danon

[11] Patent Number: 5,645,055
[45] Date of Patent: Jul. 8, 1997

[54] OXYGEN BREATHING CONTROLLER

[75] Inventor: Joseph S. Danon, Los Angeles, Calif.

[73] Assignee: Conax Florida Corporation, St. Petersburg, Fla.

[21] Appl. No.: 194,702

[22] Filed: Feb. 10, 1994

Related U.S. Application Data

[63] Continuation-in-part of Ser. No. 929,701, Aug. 12, 1992.
[51] Int. Cl.[6] .................................................... A63B 9/02
[52] U.S. Cl. ................ 128/204.25; 128/204.18; 128/205.24; 128/204.29
[58] Field of Search .................. 128/204.18, 204.16, 128/204.25, 205.24, 205.25, 204.29

[56] References Cited

U.S. PATENT DOCUMENTS

| | | | |
|---|---|---|---|
| 2,420,375 | 5/1947 | Huggenberger | 128/204.29 |
| 2,894,507 | 7/1959 | Seeler | 128/204.29 |
| 3,456,642 | 7/1969 | Cupp | 128/204.29 |
| 3,526,239 | 9/1970 | Oroza | 128/204.29 |
| 3,675,649 | 7/1972 | Basham et al. | 128/204.22 |
| 3,768,466 | 10/1973 | Johnson | 128/204.29 |
| 4,148,311 | 4/1979 | London et al. | 128/204.29 |
| 4,203,434 | 5/1980 | Brooks | 128/205.24 |
| 4,436,090 | 3/1984 | Darling | 128/205.24 |
| 4,499,914 | 2/1985 | Schebler | 128/204.29 |
| 4,648,397 | 3/1987 | Beale | 128/205.11 |
| 4,651,728 | 3/1987 | Gupta et al. | 128/204.29 |
| 4,661,124 | 4/1987 | Hamlin et al. | 55/21 |
| 4,858,606 | 8/1989 | Hamlin | 128/204.29 |
| 4,928,682 | 5/1990 | Stevenson et al. | 128/205.24 |
| 4,996,982 | 3/1991 | Williamson | 128/205.24 |
| 5,222,490 | 6/1993 | Pomerantz et al. | 128/205.24 |
| 5,241,955 | 9/1993 | Dearman et al. | 128/204.18 |
| 5,351,682 | 10/1994 | Foote | 128/205.24 |

*Primary Examiner*—Vincent Millin
*Assistant Examiner*—William J. Deane, Jr.
*Attorney, Agent, or Firm*—Hodgson, Russ, Andrews, Woods & Goodyear LLP

[57] ABSTRACT

The oxygen breathing controller of the present invention provides a first inlet regulator and a second inlet regulator. The first inlet regulator is provided with a poppet with a diaphragm around its perimeter, and the second inlet regulator is controlled by a servo pilot regulator. The oxygen breathing controller is provided with a low flow control which controls the flow of oxygen below approximately 10 lpm at altitude below 34,000 feet at suction pressure of less than 2.5 inches of water. Above 34,000 feet of altitude or breathing suction pressures of above 2.5 inches of water, the servo pilot regulator controls the second stage valving assembly.

16 Claims, 6 Drawing Sheets

OXYGEN BREATHING CONTROLLER

CROSS-REFERENCE

This application is a continuation-in-part of application Ser. No. 07/929,701 filed Aug. 12, 1992 entitled "Oxygen Breathing Controls."

FIELD OF THE INVENTION

This invention relates generally to oxygen supply systems, and more particularly to oxygen breathing controllers which supply oxygen to users in a low oxygen-level environment.

BACKGROUND OF THE INVENTION

Oxygen breathing controllers are normally used to supply oxygen to users at high altitudes. Common users are parachutists and airborne military personnel in an unpressurized aircraft. For example, a user aboard an unpressurized aircraft has the use of an oxygen supply tank, i.e., aircraft-mounted prebreather. A prebreather system supplies 100% oxygen to the user which serves to denitrify the user's blood. Utilization of the aircraft-mounted system also conserves user's personal oxygen supply for later use during a parachute descent. Before exiting the aircraft, the user switches from an aircraft-mounted prebreather to his/her personal oxygen supply.

A cabin crew member user who must perform duties during a flight may use a portable oxygen system for mobility within the aircraft cabin or may access to an aircraft-mounted prebreather to conserve oxygen in the personal supply.

Conventional controller systems have many areas that need improvement. An existing unit is CRU-79/P, which is a chest mounted, 100% oxygen, positive pressure regulator. This unit is reflective of a majority of conventional regulators using a spring-loaded diaphragm/poppet/guide/seat arrangement. Such a mechanical design has inherent problems with a leakage which is caused by a poorly-seated poppet.

Prior art breathing regulators have a problem in that approximately 10% of the volume is lost to the atmosphere. A conventional breathing regulator continuously bleeds oxygen to atmosphere even when it is not in use. The bleeding loss continues as long as the breathing regulator is connected to an oxygen source at the rate of up to 0.75 lpm. Under normal breathing conditions, a breather consumes approximately 8 lpm. Thus, a 0.75 lpm bleed rate represents a 10% volume loss to atmosphere. For a parachutist who must descend from a high altitude with a limited personal oxygen supply, a loss of 10% oxygen volume could have a significant effect.

SUMMARY OF THE INVENTION

The present invention, in a broad aspect, is an oxygen breathing controller system which is used in conjunction with an oxygen supply. The system includes a first stage regulator and a second stage regulator for initial input pressure control, and a servo regulator module and a low flow control for further pressure control before intake by a user.

The first stage regulator employs a floating poppet which squarely sits on a first stage seat assembly so that leakage and lockup pressure are reduced. Lockup pressure is a pressure at which the poppet seals on the seat with no flow through the regulator. By having a flow path through a bore of the first stage diaphragm assembly, a much larger flow area is secured as compared with conventional regulators. This results in a smaller and lighter oxygen breathing controller as a whole given the same flow requirement. Further, there are fewer moving parts, resulting in reduced cost and increased reliability. The first stage regulator and the second stage regulator together provide a two-stage input pressure control.

The low flow control is capable of two-staged delivery where 100% oxygen is supplied first and a supply diluted by the ambient air is supplied subsequently. The low flow control is provided with a pilot poppet which creates a slight leak and a slight pressure build-up in a main chamber of the oxygen breathing controller prior to inhalation by the user. A slight pressure prevents dilution of the initial flow of oxygen to the user's lungs resulting in 100% oxygen being inhaled into the most effective part of the lungs in a first phase of an inhalation event and ambient air diluted oxygen being inhaled into the top of the lungs and the trachea in a second phase of the inhalation event. This dilution of the inhaled oxygen with ambient air during the second phase of the inhalation event is referred to as phased dilution breathing.

Further, the servo regulator module of the present invention conserves oxygen by internally bleeding oxygen to the outlet chamber, and not to the atmosphere, at least up to 34,000 feet. Beyond approximately 34,000 feet, the servo regulator mechanism is taken over by the aneroid module which controls the breathing pressure schedule.

Other features and advantages will become apparent through a consideration of the detailed description herein and the accompanying drawings.

DETAILED EXPLANATION OF THE INVENTION

Figure 1:
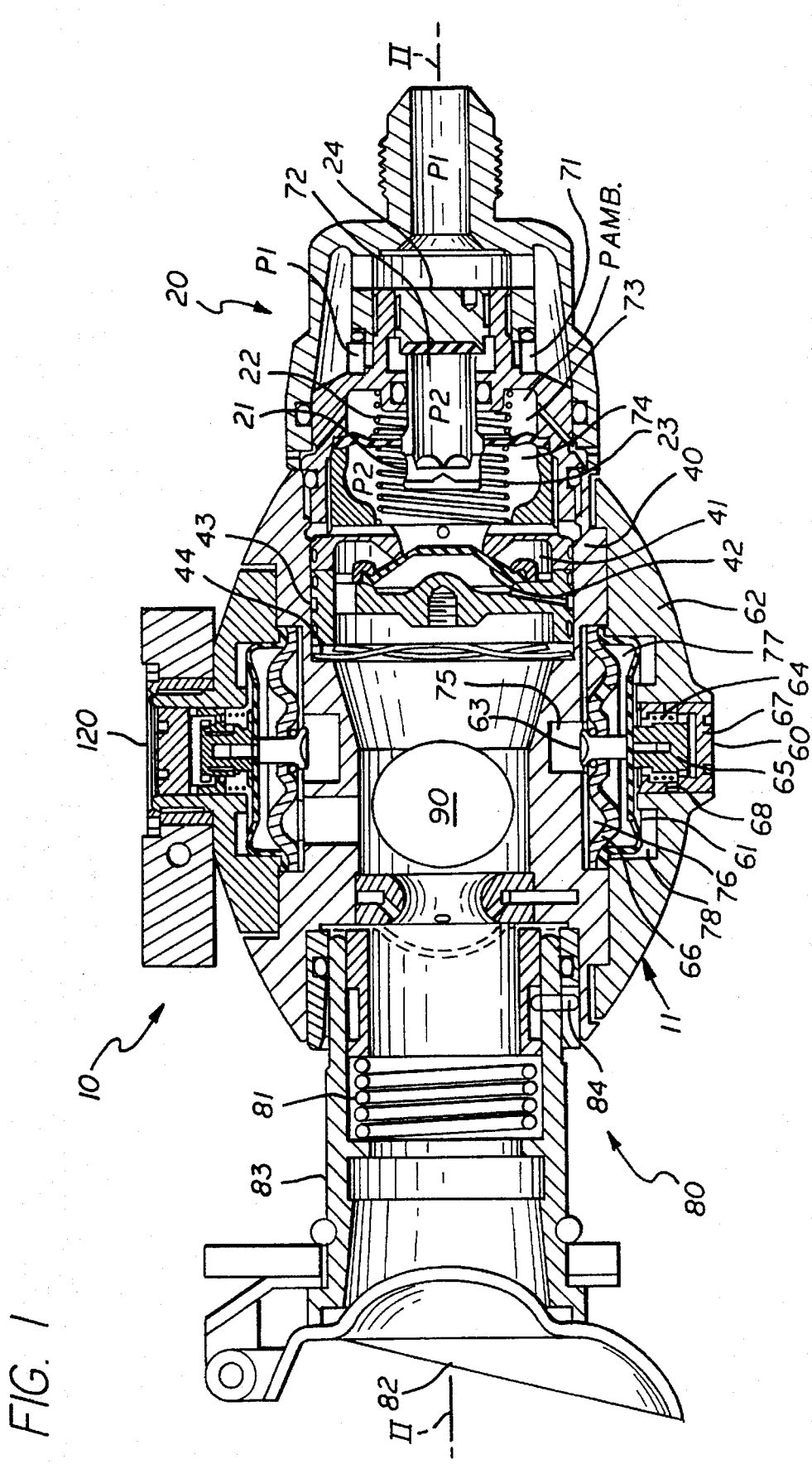
FIG. 1 shows a cross-sectional view of an oxygen breathing controller of the present invention.
Figure 2:
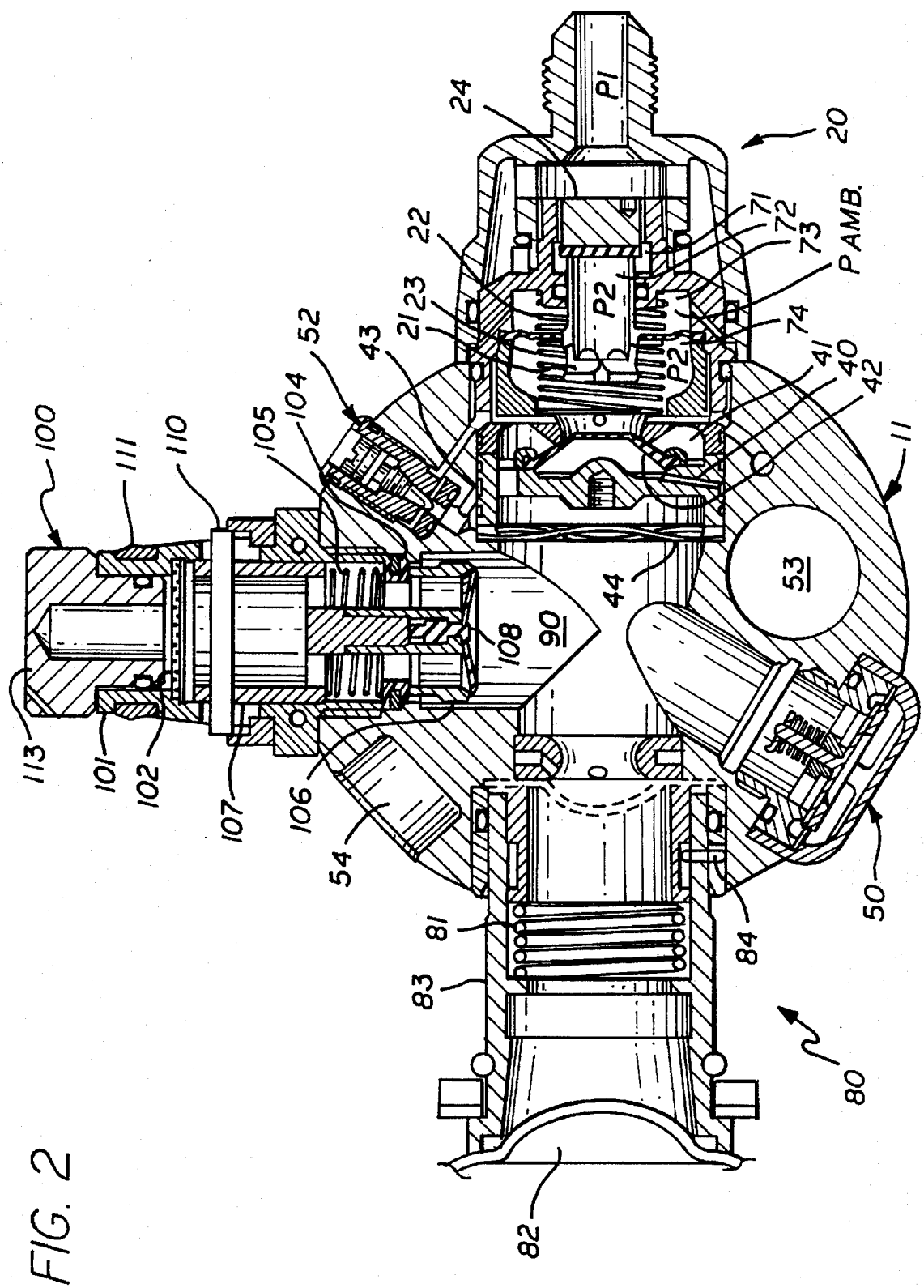
FIG. 2 shows a cross-sectional view, taken through the plane II—II of the oxygen breathing controller shown in FIG. 1.

Turning more particularly to the drawings, a cross-sectional view of the oxygen breathing controller 10 according to the present invention is shown in FIG. 1. The oxygen breathing controller 10 is provided with a main body 11 and employs a first stage regulator 20, a second stage valving assembly 40, a servo pilot regulator 60, an outer connector port adapter 80 and a low flow control 120. As can be seen, various regulators are compact modules designed around a main chamber 90. The inlet pressure is regulated by the first stage regulator 20 and the second stage valving assembly 40. The servo pilot regulator 60 and the low flow control 120 provide further control of the oxygen pressure, where the servo pilot regulator 60 in particular controls the second stage valving assembly 40. A user obtains a supply of oxygen through the outer connector port adapter 80. FIG. 2 shows a cross-sectional view of the oxygen breathing controller 10 taken along II—II line in FIG. 1.

The first stage regulator 20 shown in FIGS. 1 and 2 is provided with a floating first stage diaphragm or poppet assembly 21 which rests against a first stage seat assembly 24. Springs 22 and 23 are provided in chambers 73 and 74, respectively, and the diaphragm assembly 21 defines a chamber 72 which becomes fluidically connected with a chamber 71 when the diaphragm assembly 21 opens.

Also as shown in FIGS. 1 and 2, the second stage valving assembly 40 is mounted as an integral part of the main body 11 and is housed in an outlet housing 43. A flexible second stage diaphragm 42 may rest against or away from a seat of a diaphragm cage 41 depending on the flow of oxygen. On the downstream side of the second stage valving assembly 42, wave washers 44 are employed. The outlet housing 43 is designed to support the diaphragm 42 without stretching it, thereby preventing overstress of the diaphragm 42.

As shown in FIG. 1, the servo pilot regulator 60 employs a pilot seal plate 66 and a diaphragm plate assembly 61, both coupled with a pilot poppet 63. The pilot seal plate 66 abuts a chamber 75 and defines chambers 76 and 77. A chamber 78 is defined by an upper pilot cover 62. A spring 64 is held by a spring adjustment holder 65 topped by a pilot cap seal 67, and the spring adjustment holder 65 is provided with an adjustment screw 68. The servo pilot regulator 60 as shown in FIG. 1 is in its unpressurized state.

The outlet connector port adaptor 80 shown in FIGS. 1 and 2 serves to attach an oxygen mask inlet hose to the oxygen breathing controller 10. The outlet connector port adaptor 80 plugs into the main body 11 via a 3-pin spring loaded fitting, and is shown having a cover assembly 82 and an outlet housing 83. The outlet connector port adaptor 80 is held in place in the main body 11 with a bayonet fitting that is locked in place with a downward push and a slight clockwise twist of the fitting. The locking action is accomplished by a pin 84 being twisted into a slot and then held in place by a spring 81. To disconnect the outlet connector port adaptor 80, the unit is pushed inward and twisted slightly in the counterclockwise direction.

The prebreathing adaptor assembly 100 shown in FIG. 2 may be connected to the on-board prebreather oxygen supply to conserve the user's personal oxygen supply. The prebreather supply connection is slipped over the inlet fitting of the prebreathing adaptor assembly 100 until it snaps in place over a retaining ring 111. When the prebreather is fitted on the prebreathing adaptor assembly 100, it pushes a pin spring 110, thereby compressing a compression spring 105. This moves an inlet piston 107 which in turn moves a sealing grommet 104 from the sealing surface of an adaptor 101 to open the assembly 100. A dust cap 113 is shown plugged into the inlet port of the assembly 100 to prevent inhalation of smoke or other contamination. If the dust cap 113 is removed and the assembly 100 is not connected to the on-board oxygen supply, a check leaf 108 serves as a diluter valve by sealing against an inlet valve seat 106 to prevent leakage. A course screen 102 prevents contamination of the diluted supply by comparatively large particles of contamination. Where the pressure in the cavity downstream of the second stage valving assembly 40 is above the cracking pressure of the check leaf 108, which is approximately 0.2 inches of water, it lifts off the seat to allow ambient air to enter to prevent suffocation.

As shown in FIG. 2, two cavities 53 and 54 are provided in the main body 11. The cavity 53 is designed to accept an aneroid assembly 140 shown in FIG. 4. The dust cap cavity 54 is a cavity for a dust cap which is used to block a diluter valve to prevent contamination of the oxygen flow during operations in contaminated or smoke filled cabin atmospheres.

Figure 3:
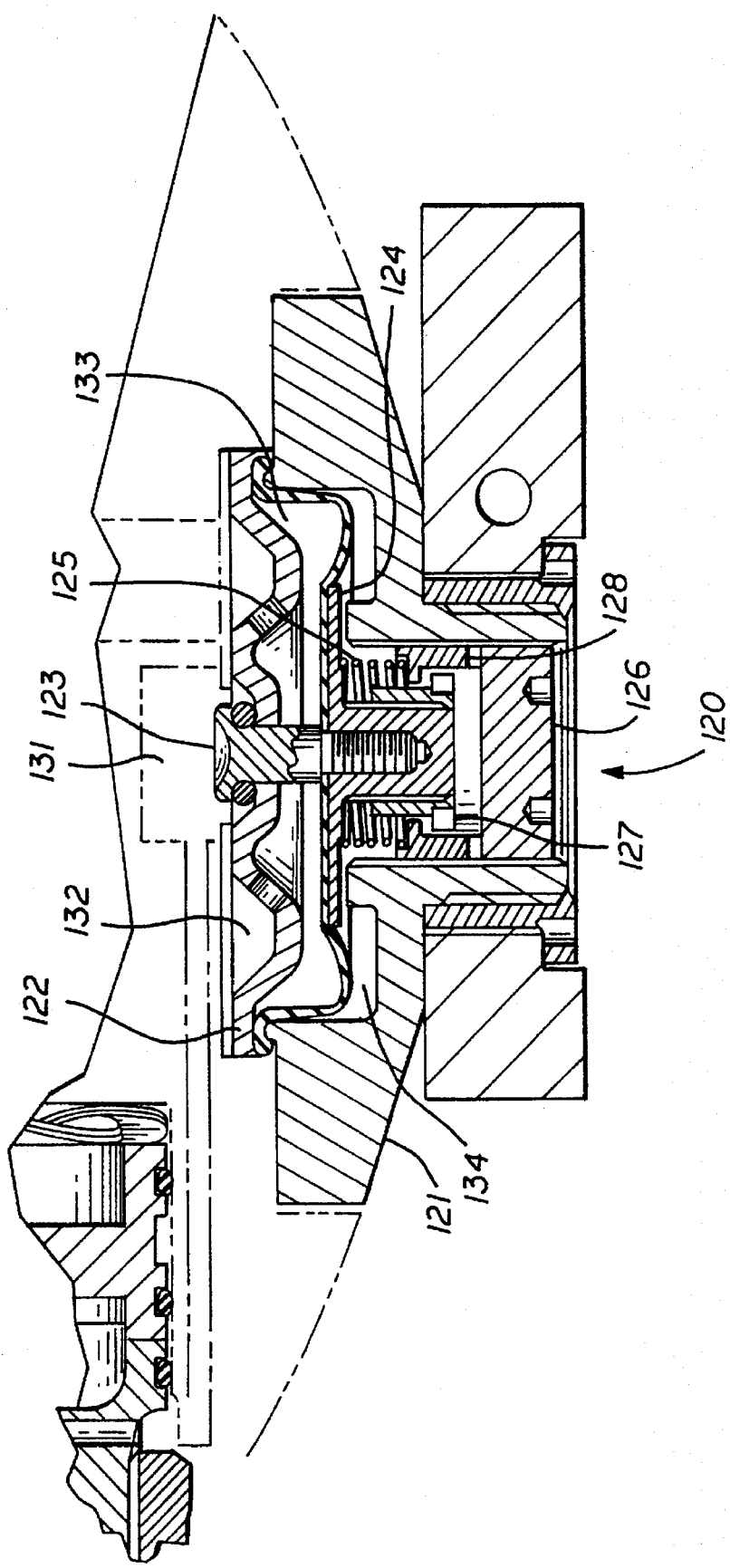
FIG. 3 is a cross-sectional view of a low flow control.

The low flow control 120, which is shown closed in FIG. 3, employs a pilot poppet 123 which is coupled with a pilot plate seal 122 and a pilot diaphragm 124 and abuts a spring 125 and a spring adjustment holder 127. The low flow control 120 is housed partially by a lower pilot cover 121 and topped with a lower pilot cap 126. An adjustment screw 128 is provided for calibrating the pilot poppet 123. A chamber 133 is defined between the pilot plate seal 122 and the pilot diaphragm 124, and is fluidically connected with a chamber 132. A chamber 134 is defined by the pilot diaphragm 124 and the spring adjustment holder 127 and is vented to ambient.

Figure 4:
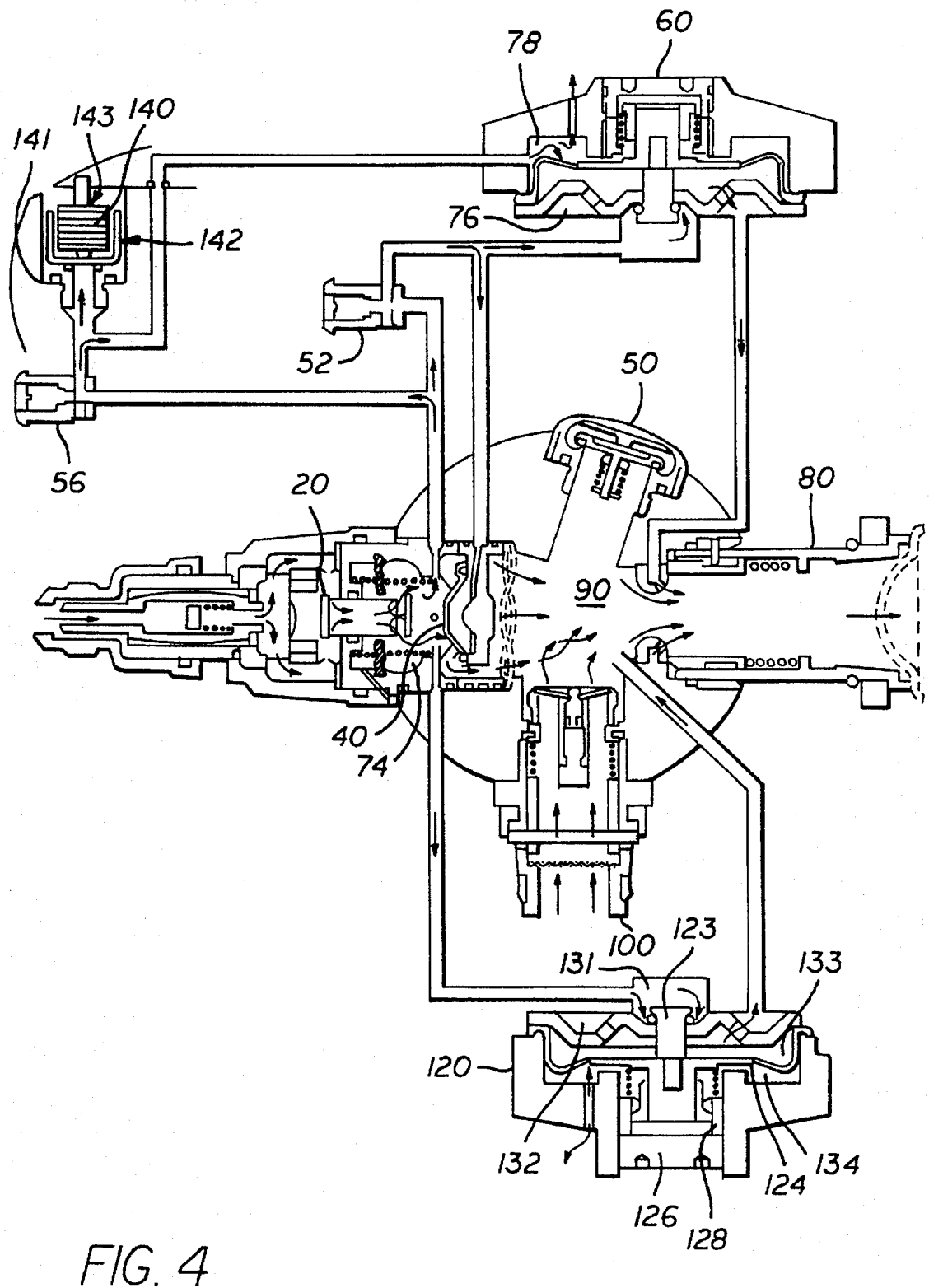
FIG. 4 shows a functional schematic of the oxygen breathing controller.

In FIG. 4, flow restrictors 52 and 56 serve as adjustable orifices in the oxygen breathing controller 10. The flow restrictor 52 is disposed between the second stage valving assembly 40 and the servo pilot regulator 60. The other flow restrictor 56 is disposed upstream of the aneroid assembly 140 for its adjustment. The aneroid assembly 140 employs an aneroid poppet 142 held firmly against an aneroid seat 141 by an aneroid element 143.

FIG. 4 provides a functional schematic of the major components of the oxygen breathing controller 10. Operation at normal sea level is explained below. Where there is no breathing demand, as oxygen pressure is applied to the inlet of the oxygen breathing controller, as the oxygen pressure increases above approximately 5 psig which is the set point of the first stage regulator 20, the latter moves from its static open position to a fully closed position. Where there is a demand, the low flow controller 120 opens to allow approximately 8 to 10 lpm of oxygen to pass to the main chamber 90. The initial flow of oxygen is at a slight positive pressure due to the function of the low flow controller 120 as explained later.

During this cycle, if the breathing demand is more than 8 to 10 lpm and the breathing suction is between −0.2 inches of water and −2.0 inches of water, ambient air will be drawn through the prebreathing adaptor assembly 100 to dilute the oxygen flow. However, at the same time the required 8 to 10 lpm is supplied to the user. At this time, the second stage valving assembly 40 and a relief valve 50 are closed. The aneroid assembly 140 is in the sea level condition where the minimum force is exerted between the aneroid seat 141 and the aneroid poppet 142. The control flow to the aneroid assembly 140 which passes through the restrictor 56 is vented to ambient through the aneroid assembly 140 and does not affect the set point of the servo pilot regulator 60. The aneroid assembly 140 does not affect the operation of the oxygen breathing controller 10 below an ambient altitude of 34,000 feet.

The first stage regulator 20 shown in FIGS. 1 and 2 regulates the oxygen pressure from an inlet pressure of 50 psig to a nominal 5 psig in a single stage. The diaphragm assembly 21 assumes an open position if the inlet pressure P1 of the chamber 71 is zero. The chamber 73 remains at ambient pressure Pamb while the diaphragm assembly 21 stays open. The second stage valving assembly 40 is closed if the pressure P2 in the discharge chamber 74 becomes zero. Under the condition, the pressures P1 and P2 in the chambers 71 and 72, respectively, are equal.

If P1 increases, P2 increases correspondingly since the diaphragm assembly 21 moves off the first stage seat assembly 24, thereby opening the flow passage. When the inlet pressure P1 reaches approximately 5 psig, the discharge pressure P2 of the first stage regulator 20 also reaches approximately 5 psig. The diaphragm assembly 21 is substantially in balance since the closing force is equal to the opening force. As P1 increases and P2 is increased, the closing force overcomes the opening force. The closing force on the downstream side of the diaphragm assembly 21 is equal to P2 times its area upon which the pressure difference between P2 and Pamb acts. The opening force is equal to P1 times the cross-sectional area of the inlet tube of the diaphragm assembly 21.

Where there is no breathing demand, the first stage regulator 20 and the second stage valving assembly 40 are closed. If there is an oxygen demand of below 8 to 10 lpm, the pressure P2 in the discharge chamber 74 decreases and as P2 decreases below the set point of the first stage regulator 20, the force balance on the diaphragm assembly 21 is upset, thereby allowing oxygen to flow from the chamber 71 through a bore of the first diaphragm assembly 21 into the chamber 72 and the discharge chamber 74. The increase in the pressure P2 in the discharge chamber 74 restores the balance of the first stage diaphragm assembly 21 at approximately 5 psig, thereby regulating the pressure.

As shown in FIGS. 1 and 2, when the second stage valving assembly 40 is fully closed, the servo pilot regulator 60 is closed, and the outlet pressure to the flow restrictor 52, the inlet pressure to the servo pilot regulator 60, is equal to the control pressure of the servo pilot regulator 60. Thus, the pressures on both sides of the second stage diaphragm 42 are equal, and the diaphragm 42 is pressed against the valve seat of the diaphragm cage 41 by the elastic memory force of the second stage diaphragm 42.

If the outlet pressure of the second stage valving assembly 40 decreases to below the pressure set point demanded by the servo pilot regulator 60, indicating a breathing demand of above 8 to 10 lpm, the control pressure of the servo pilot regulator 60 decreases so that there is a pressure difference across the second stage diaphragm 42. The second stage diaphragm 42 then lifts off the integral seat of the diaphragm cage 41, thereby creating a flow through the second stage valving assembly 40. During normal pressure control, the second stage diaphragm 42 is in an intermediate position between the fully closed position and the fully open position against the outlet housing 43. When the altitude is below 34,000 feet, the oxygen flow rate is below 8 to 10 lpm, and the breathing suction pressure is less than 2.5 inches of water (pressures greater than −2.5 inches of water), the low flow control 120 meets the oxygen demand, and the second stage valving assembly 40 is closed.

At altitudes above 34,000 feet, the aneroid assembly 140 serves to adjust the breathing schedule of the second stage valving assembly 40 by bleeding oxygen to atmosphere and changing the set point of the servo pilot regulator 60. As the altitude increases, the aneroid element 143 expands and bleeds less oxygen. This increases the control pressure to the servo pilot regulator 60, thereby providing oxygen to the user at a predetermined schedule. Scheduled pressure is obtained with no or extremely small relative motion between the aneroid poppet 142 and the aneroid seat 141. The flow of oxygen through the aneroid assembly 140 from its inlet to vent is a controlled leak.

When the suction pressure is less than approximately 2.5 inches of water (greater than −2.5 inches of water) in the venturi throat downstream of the second stage valving assembly 40, the pressures in the chambers 76 and 77 do not generate sufficient force on the diaphragm plate assembly 61 to overcome the force generated by the spring 64, and the pilot poppet 63 remains on its seat. This prevents flow through the servo pilot regulator 60 to the second stage valving assembly 40, and the latter is kept closed. As the breathing rate increases due to either increased exertion or hyperventilation, and the suction pressure in the venturi reaches 2.5 inches of water (less than −2.5 inches of water), the pressures in the chambers 76 and 77 decrease to let the flow through the pilot poppet 63 to the restrictor 52. The pressure in the chamber 75 then decreases as well as the pressure behind the diaphragm 42, and it causes the second stage valving assembly 40 to open and supply oxygen flow. In this way, the servo pilot regulator 60 controls the second stage valving assembly 40 so that a suction pressure of 2.5 inches of water is maintained until the flow through the venturi starts to choke.

At this point, the pressure supplied to the user increases as the flow increases due to an increased demand. At about 34,000 feet or higher, the expansion of the aneroid element 143 is enough to decrease its bleeding to ambient through the aneroid poppet 142, and the aneroid assembly 140 starts to bleed pressure into the chamber 78 of the servo pilot regulator 60. As the altitude increases, the pressure in the chamber 78 increases requiring a greater pressure in the chamber 76 in order to open the pilot poppet 63. Since the pressure in the chamber 76 is the pressure downstream of the second stage valving assembly 40, it is regulated to a higher pressure as the altitude increases. The regulated oxygen pressure in a main chamber 90 is approximately 20 inches of water at 45,000 feet due to the effect of the aneroid assembly 140 on the servo pilot regulator 60.

The relief valve 50 provides overpressure protection for the user's lungs regardless of altitude level. If the second stage valving assembly 40 malfunctions, the pressure in the main chamber 90 is relieved by the relief valve 50, which starts to open at an internal pressure of 20 inches of water and fully opens at 26 inches of water with a flow capacity of 250 slpm.

The low flow control 120 regulates all oxygen where the required flow is approximately 8 to 10 lpm, the altitude is below approximately 34,000 feet and the oxygen supply suction pressure is less than 2.5 inches of water (greater than −2.5 inches of water). If the required flow rate is above 8 to 10 lpm, the flow is diluted with ambient air an below altitude of approximately 34,000 feet and breathing suction pressures of less than 2.5 inches of water (greater than −2.5 inches of water) by the prebreathing adaptor assembly 100.

When the pressure downstream of the first stage regulator 20 increases to its regulated value of approximately 5 psig, the pressure in the chamber 131 increases. Where there is no breathing demand, the pressure in the chamber 133 is equal to or greater than ambient pressure, and equal to that of the main chamber 90. The pressure of the chamber 134 is ambient pressure, and the pressure force on the pilot diaphragm 124 holds the pilot poppet 123 in the closed position.

The low flow control 120 provides slightly pressurized 100% oxygen at the start or first phase of an inhalation event and subsequently provides oxygen diluted by ambient air in a second phase of the inhalation event. This phased dilution breathing is a unique feature of the low flow control 120 where the bottom of the lungs is filled with 100% oxygen in the first phase of inhalation, and dilution occurs only in the upper portion of the lungs and in the trachea in the second phase of inhalation, thereby allowing maximum utilization of the oxygen by the body. This phased dilution manner of breathing also contributes to conservation of oxygen supply. If the oxygen breathing controller 10 is torso-mounted rather than mask-mounted, oxygen first inhaled by the user is what is left in the hose from the last breathing cycle, which may or may not be 100% oxygen.

The slight positive pressure at the start of the inhalation is provided as follows. The adjustment screw 128 of the low flow control 120 is adjusted so that the pilot poppet 123 slightly leaks to allow oxygen to flow through the poppet 123 into the chamber 133, to the chamber 132 through the holes in a poppet plate seal 122 and finally to the main chamber 90, raising the pressure of the main chamber 90. The flow occurs with no demand.

As the breathing is initiated, the slightly pressured main chamber 90 is depressurized. The chamber 133 is also depressurized which changes the force balance on the pilot diaphragm 124 and causes the diaphragm 124 to open the pilot poppet 123, thereby initiating flow through the poppet 123. The oxygen flow can be controlled to a flow rate of 1 to 10 lpm by the low flow control 120. This supplies all of the required oxygen at a normal breathing rate below an altitude of approximately 34,000 feet. Since the oxygen temperature is constant, the flow is a function of the delta held constant at 8 to 10 lpm. The pressure drop from the inlet to the chamber 131 of the flow control 120 to the main chamber 90 stays substantially constant during an inhalation by the user.

Figure 5:
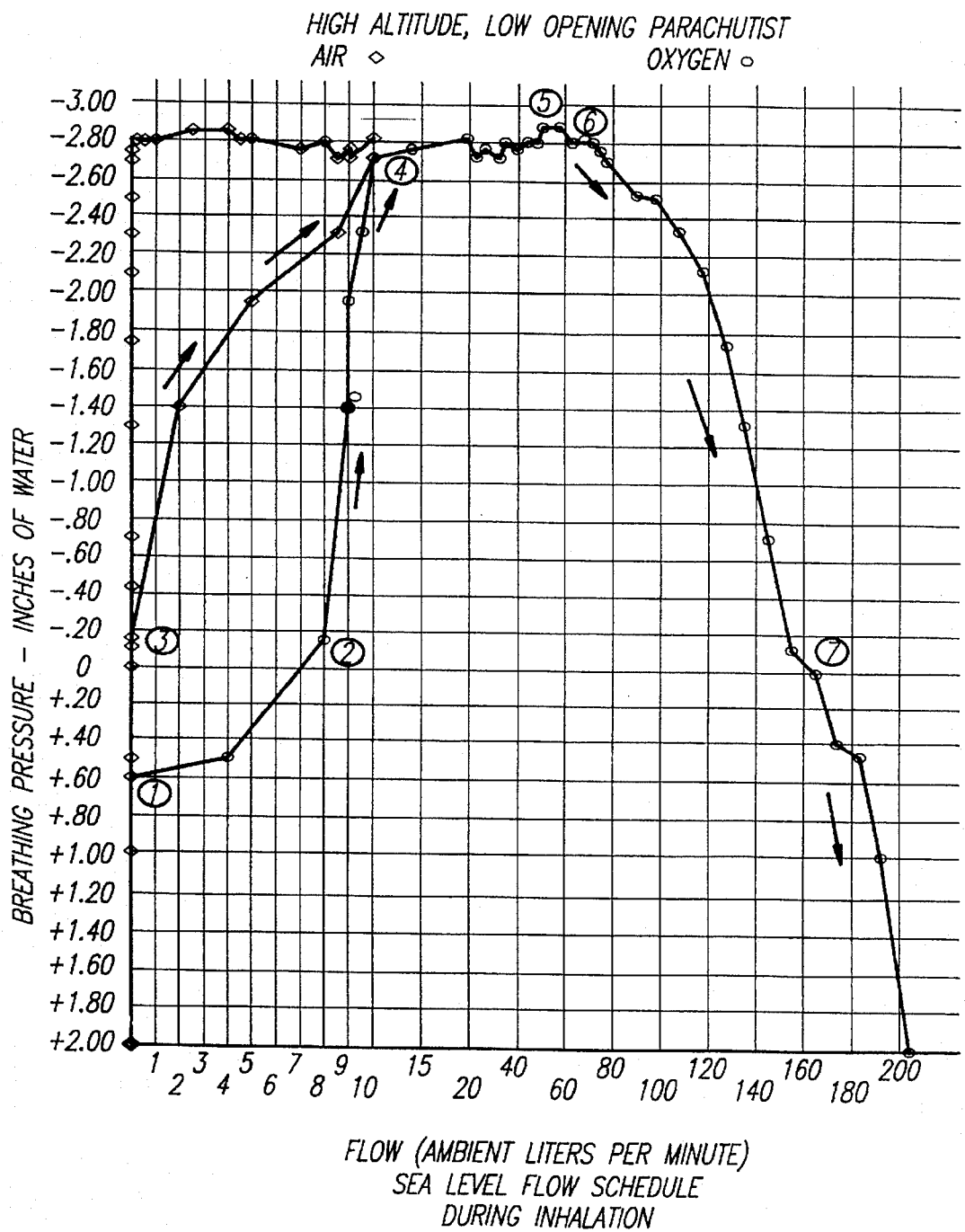
FIG. 5 is a diaphragm showing a relationship between breathing pressures and flow.

FIG. 5 shows a sea level flow schedule during inhalation. The schedule represents inhalations from very shallow breathing up to very deep, possibly rapid breathing, for instance, during hyperventilation. During a normal inhalation, the oxygen flow starts at point (1) on the oxygen curve. A slight positive pressure is provided during the inhalation of the breath until the flow increases to 8 lpm indicated by point (2). At this flow rate, there is no ambient air flow as shown by point (3). If the inhalation continues, ambient air is mixed with the oxygen flow in the previously described phased dilution manner. A normal breath can generate −1.4 inches of water suction and would result in a flow of 9 lpm of oxygen and 2 lpm of ambient air as shown. Thus, a total flow of 11 lpm of diluted oxygen is supplied to the user during inhalation. Note that the schedule does not show the time required by the breather to make an inhalation. It only shows the flow and the pressure.

A deeper inhalation moves further up both the oxygen and the ambient air curve of the schedule. As a breath becomes deeper, the flow moves up the curve to point (4) at which point the oxygen flow and the ambient air flow are equal at 10 lpm for a total diluted oxygen flow of 20 lpm. All oxygen is still supplied by the low flow controller 120 during this inhalation period. The ambient air flow will be supplied by the diluter function of the prebreathing adaptor assembly 100 in the phased dilution manner.

If the user hyperventilates at sea level, and the oxygen flow requirement is greater than 10 lpm as well as the suction pressure of greater than −2.5 inches of water, the capacity of the low flow controller 120 does not meet the demand any longer. The second stage valving assembly 40 opens instead to supply the oxygen flow in response to a control signal from the servo pilot regulator 60. As this occurs, diluter control portion of the prebreathing adaptor assembly 100 is forced to close as the ambient air flow drops from point (4) to point (5). The oxygen flow increases to meet the demand.

If the demand is greater than approximately 80 slpm, the combination of the servo pilot regulator 60 and the second stage valving assembly 40 increases the supply pressure as the flow demand increases. At an oxygen flow of approximately 170 slpm, the supply pressure becomes positive and at the maximum flow of 200 slpm, the oxygen is supplied at a positive pressure of +2.0 inches of water.

Figure 6:
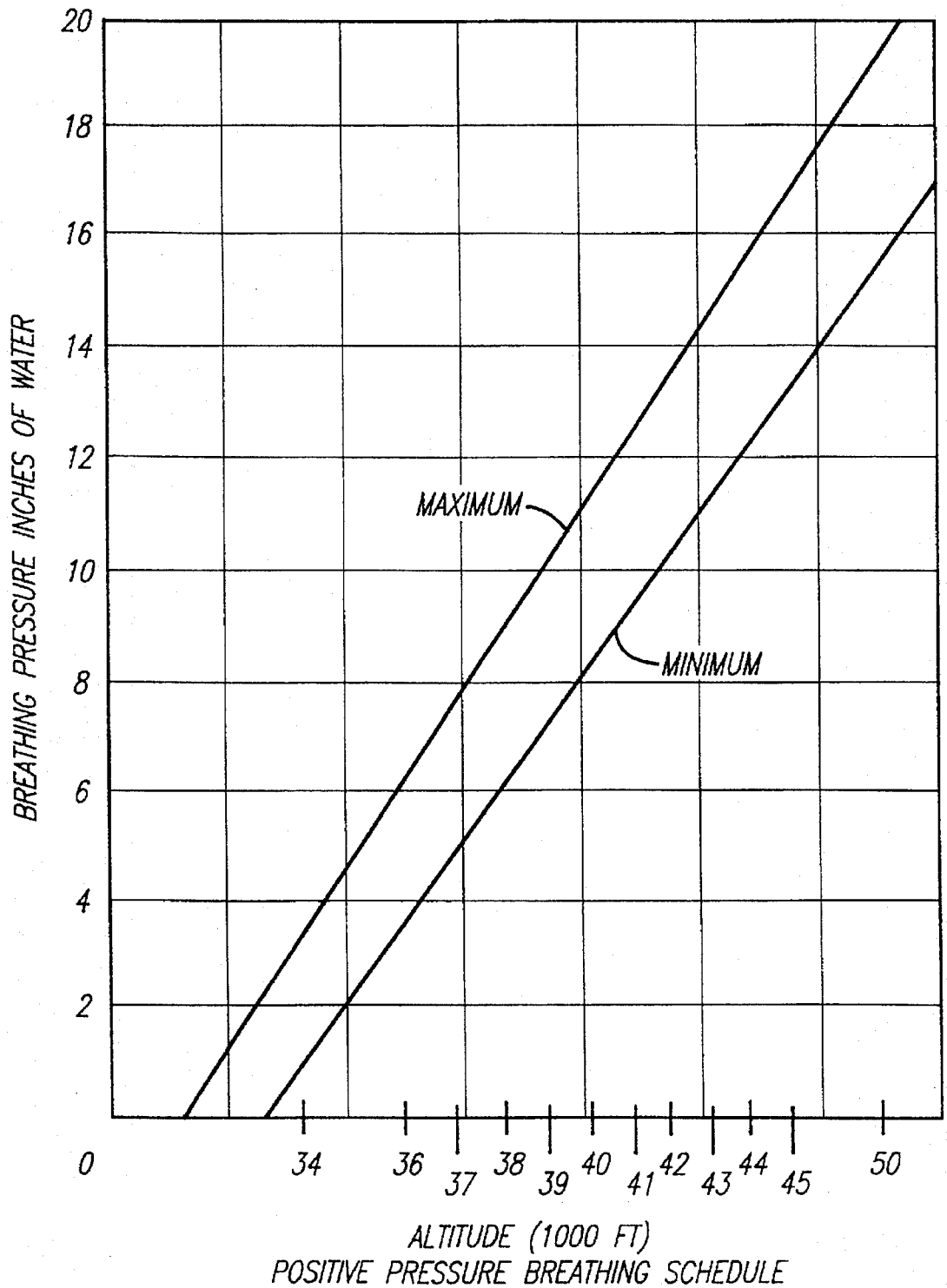
FIG. 6 shows a positive pressure breathing schedule.

The operation of oxygen breathing controller remains unchanged from sea level to 34,000 feet ambient altitude. The oxygen flow and the diluter flow is as shown in FIG. 5. At 34,000 feet altitude, the aneroid assembly 140 starts to bias the servo pilot regulator 60. This results in the second stage valving assembly 40 regulating to a higher pressure which prevents ambient air from entering through the diluter function of the prebreathing adaptor assembly 100. As the ambient altitude increases, the combination of the aneroid assembly 140, the servo pilot regulator 60 and the second stage valving assembly 40 increases the oxygen supply pressure as a function of altitude as shown in FIG. 6.

At altitudes above 34,000 feet, the aneroid assembly 140 in FIG. 4 biases the servo pilot regulator 60 such that the oxygen breathing controller provides 100% oxygen at a positive pressure. The positive pressure shuts the diluter function of the prebreathing adaptor assembly 100. Note that the controller provides oxygen at a decreased partial pressure due to altitude effects but the volume remains constant. Further, in the event of hyperventilation, the increased demand is met according to the schedule.

Having described the preferred embodiment of the oxygen breathing controller according to the present invention, it should be apparent that various additional objects and advantages have been attained by the present invention and that a variety of modifications can be made within scope and spirit of the present invention.

What is claimed is:

1. A breathing controller means connected to a breathable gas supply and an ambient air supply for regulating flow of the breathable gas and the ambient air to a user in a phased dilution manner during successive inhalation events, which comprises:

a) first means for supplying the user with substantially 100% oxygen as the breathable gas during a first phase of an inhalation event; and b) second means for diluting the substantially 100% oxygen with the ambient air during a second phase of the said inhalation event to thereby provide the breathing gas and the ambient air to the user in the phased dilution manner so that during a first phase of the inhalation event, substantially 100% oxygen is inhaled into a respiratory portion of the lungs and during a second phase of the said inhalation event, the ambient air diluted oxygen fills into a conducting portion of the respiratory system, the conducting portion leading to the respiratory portion of the lungs, and wherein during a next successive inhalation event, the breathing controller means again provides the breathing gas and the ambient air to the user in the phased dilution manner.

2. The breathing controller means of claim 1 wherein the first means includes means for providing a slight bleed through the regulator.

3. The breathing controller means of claim 1 wherein the first means for supplying the user with substantially 100% oxygen comprises:

a) a first regulator means provided to regulate the breathable gas from a first pressure to a reduce, set point pressure;

b) a second regulator means coupled to the first regulator means and disposed downstream thereof, the second regular means comprising:
      i) an inlet chamber in fluid flow communication with the breathable gas at the reduced, set point pressure;
      ii) an outlet chamber disposed downstream of the inlet chamber; and iii) a diaphragm means separating the inlet chamber and the outlet chamber of the second regulator means; and c) a servo regulator means coupled to the second regulator means for regulating a pressure differential across the inlet chamber and the outlet chamber of the second regulator means according to an altitude dependent breathing requirement.

4. The breathing controller means of claim 3 further comprising means for controlling a minimum pressure limit with respect to altitude.

5. The breathing controller means of claim 1 wherein the first means for supplying the user with substantially 100% oxygen comprises:

a) a first regulator means provided to regulate the breathable gas from a first pressure to a reduced, set point pressure; and b) a second regulator means coupled to the first regulator means and disposed downstream thereof, the second regulator means comprising:
   i) an inlet chamber in fluid flow communication with the breathable gas at the reduced, set point pressure:
   ii) an outlet chamber disposed downstream of the inlet chamber;
   iii) a diaphragm means separating the inlet chamber and the outlet chamber of the second regulator means; and
   iv) means for selectively creating a pressure differential across the inlet chamber and the outlet chamber of the second regulator means and for flexing the diaphragm means between a closed, no flow position and an open, flow position to provide the breathable gas to the user upon the occurrence of the inhalation event.

6. The breathing controller means of claim 5 wherein the means for selectively creating a pressure differential includes an aneroid means which regulates the pressure differential across the inlet chamber and the outlet chamber of the second regulator means based on altitude, and wherein when the altitude is above an altitude threshold, the higher the altitude, the greater the pressure differential required to flex the diaphragm means towards the open position to thereby increase the pressure of the breathable gas at the outlet chamber of the second regulator means.

7. The breathing controller means of claim 5 further comprising means for shutting the fluid flow during exhalation.

8. The breathing controller means of claim 5 further comprising a flow restrictor means for restricting the fluid flow between the inlet chamber and the outlet chamber of the second regulator means.

9. A breathing controller means for supplying a breathable gas and ambient air to a user's respiratory system in a phased dilution manner during successive inhalation events, the breathing controller means comprising:

a) a first regulator means for regulating a pressure of substantially 100% oxygen as the breathable gas from a first pressure to a reduced, set point pressure;

b) a low flow control means for supplying the breathable gas to the user at a breathing flow rate less than a breathing inhalation quantity threshold; and c) means for diluting the substantially 100% oxygen with ambient air when the user's breathing requirements are greater than the breathing inhalation quantity threshold, wherein the means for diluting is actuatable to provide the breathing gas and the ambient air to the user in the phased dilution manner so that during a first phase of an inhalation event, the substantially 100% oxygen is inhaled into respiratory portion of the lungs and during a second phase of the said inhalation event, the ambient air diluted oxygen fills into a conducting portion of the respiratory system, the conducting portion leading to the respiratory portion of the lungs and wherein during a next, successive inhalation event, the means for diluting is actuatable when the user's breathing requirements are greater than the breathing inhalation quantity threshold to again provide the breathing gas and the ambient air to the user in the phased dilution manner.

10. The breathing controller means of claim 9 wherein the first means for regulating the substantially 100% oxygen comprises:

a) a first regulator means provided to regulate the breathable gas from a first pressure to a reduce, set point pressure; and b) a second regulator means coupled to the first regulator means and disposed downstream thereof, the second regulator means comprising:
   i) an inlet chamber in fluid flow communication with the breathable gas at the reduced set point pressure;
   ii) an outlet chamber disposed downstream of the inlet chamber;
   iii) a diaphragm means separating the inlet chamber and the outlet chamber of the second regulator means; and
   iv) means for selectively creating a pressure differential across the inlet chamber and the outlet chamber of the second regulator means and for flexing the diaphragm means between a closed, now flow position and an open, flow position to provide the breathable gas to the user upon the occurrence of the inhalation event.

11. The breathing controller means of claim 9 wherein the first means for supplying the substantially 100% oxygen comprises:

a) a first regulator means provided to regulate the breathable gas from a first pressure to a reduced, set point pressure;

b) a second regulator means coupled to the first regulator means and disposed downstream thereof, the second regulator means comprising:
   i) an inlet chamber in fluid flow communication with the breathable gas at the reduced, set point pressure;
   ii) an outlet chamber disposed downstream of the inlet chamber;
   iii) a diaphragm means separating the inlet chamber and the outlet chamber of the second regulator means; and c) a servo regulator means coupled to the second regulator means for regulating a pressure differential across the inlet chamber and the outlet chamber of the second regulator means according to an altitude dependent breathing requirement.

12. The breathing controller means of claim 10 wherein the means for selectively creating the pressure differential across the inlet chamber and the outlet chamber of the second regulator means includes an aneroid means in fluid flow communication with the second regulator means, the aneroid means comprising an aneroid chamber defining a flow opening in one wall and a vent opening in another wall; a bleed stem disposed in the flow opening in the aneroid chamber, wherein when the altitude is below an altitude threshold, a portion of the oxygen flow from the inlet chamber of the second regulator means flows through the vent opening; and a control aneroid disposed in the aneroid chamber, wherein the control aneroid expands and displaces the bleed stem in the flow opening in response to an increase in altitude above the altitude threshold thereby permitting a greater quantity of the breathable gas to flow between the inlet chamber and the outlet chamber to increase the pressure differential across the inlet chamber and the outlet chamber of the second regulator means, and wherein when the altitude is above the altitude threshold, the higher the altitude, the greater the pressure differential required to flex the diaphragm means towards the open position to thereby increase the pressure of the breathable gas at the outlet chamber of the second regulator means.

13. The breathing controller means of claim 11 further comprised of means for controlling a minimum pressure limit with respect to altitude.

14. A method for regulating flow of a breathable gas and ambient air to a user's respiratory system during an inhalation event, comprising the steps of:
   a) regulating the breathable gas from a first pressure to a breathable pressure;
   b) supplying the user with the substantially 100% oxygen as the breathable gas during a first phase of the inhalation event thereby filling a respiratory portion of the user's lungs with the substantially 100% oxygen during the first phase;
   c) diluting the substantially 100% oxygen with ambient air during a second phase of the said inhalation event in the dilution manner thereby filling the ambient air diluted oxygen into a conducting portion of the respiratory system, the conducting portion leading to the respiratory portion of the lungs; and
   d) regulatory flow of the breathing gas and the ambient air to the user in the phased dilution manner during a next, successive inhalation event.

15. The method of claim 14 including regulating the breathable gas from the first pressure to the breathable pressure at a generally constant flow rate in two stages upon the occurrence of the inhalation event.

16. A method for regulating flow of a breathable gas and ambient air to a user's respiratory system a phased dilution manner during successive inhalation events comprising the steps of:
   a) supplying the user with substantially 100% oxygen as the breathable gas during a first phase of an inhalation event thereby filling a respiratory portion of the user's lungs with the substantially 100% oxygen during the first phase;
   b) diluting the substantially 100% oxygen with the ambient air during a second phase of the said inhalation event in the phased dilution manner thereby filling the ambient air diluted oxygen into a conducting portion of the respiratory system, the conducting portion leading to the respiratory portion of the lungs; and
   c) regulating flow of the breathable as and the ambient air to the user in the phased dilution manner during a next, successive inhalation event.

* * * * *